Figure 4:
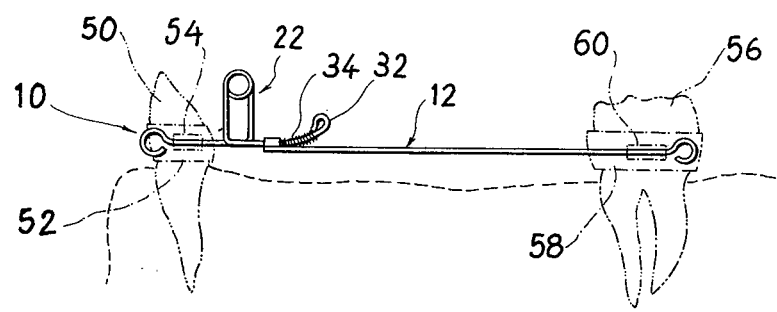

United States Patent [19]

Ladanyi

[11] 4,255,139
[45] Mar. 10, 1981

[54] ORTHODONTIC APPLIANCE

[76] Inventor: Csaba Ladanyi, Bahnhofstrasse 6, DM 7530 Pforzheim, Fed. Rep. of Germany

[21] Appl. No.: 942,307

[22] Filed: Sep. 14, 1978

[30] Foreign Application Priority Data

Sep. 17, 1977 [DE] Fed. Rep. of Germany ....... 7728871

[51] Int. Cl.³ .............................................. A61C 7/00
[52] U.S. Cl. .................................................. 433/21
[58] Field of Search ........................... 32/14 R; 433/21

[56] References Cited

U.S. PATENT DOCUMENTS

| 2,580,042 | 12/1951 | Paus ..................................... 32/14 A |
| 3,641,672 | 2/1972 | Kesling ................................ 32/14 A |

*Primary Examiner*—Robert Peshock
*Attorney, Agent, or Firm*—Bernard & Brown

[57] ABSTRACT

The invention relates to a retractor for the correction of dental misplacement comprising two wire members overlapping each other and displaceable relative to each other in a longitudinal direction against the action of a helical pressure spring, the first of said wire members carrying said pressure spring between the end overlapping the second wire member and a guiding member comprising an opening to hold said guiding member displaceably on said first wire member, and said second wire member being displaceably guided along said first wire member by means of said guiding member which is in the form of a tube.

7 Claims, 4 Drawing Figures

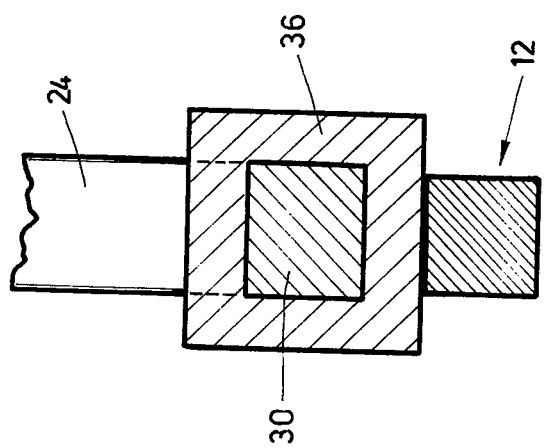
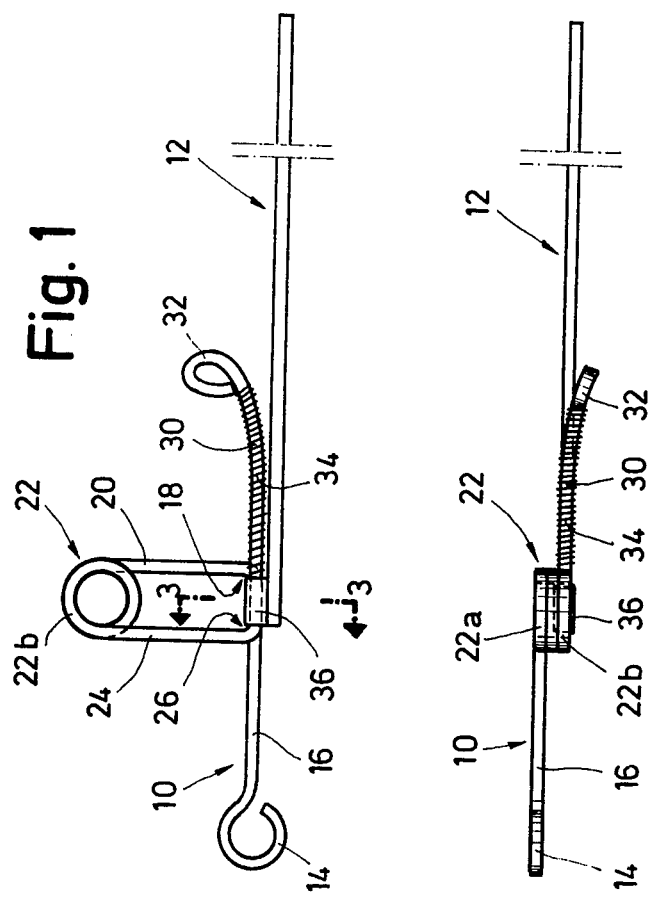

ORTHODONTIC APPLIANCE

BACKGROUND AND DISCUSSION OF THE INVENTION

Retractors serve to pull a tooth in a certain direction by exerting a tractive force, or to tilt a tooth by exerting a torque so as to correct dental misplacement. A first known retractor consists of a single wire member which—starting from one end—is first of all bent towards one side at an approximate right angle, then forms a spring with one turn (3×180°) and subsequently extends with one wire portion beyond the longitudinal axis of the retractor to the upper side, where the wire forms two loops oriented in the direction of the reactor ends. The wire then extends beyond the longitudinal axis of the retractor again to form over the aforementioned spring a second identical spring, from which the wire extends back to the longitudinal axis of the retractor and after making a bend of approximately 90° forms the continuation of this longitudinal axis. In order to obtain the necessary spring path, the wire portions of this known retractor that lead to the spring turns must be relatively long, and, in addition, wire turns are located beyond, i.e., on either side of the longitudinal axis of the retractor. For this reason, this known retractor is extremely vulnerable to becoming distorted in shape, for example, by the tooth brush when the teeth are being cleaned. Furthermore, it is annoying to have parts of the retractor protruding on either side of the longitudinal axis of the retractor. Finally, the known retractor is rather unstable in the face of torsional stress, which has a negative effect on the accuracy of the dental misplacement correction.

A retractor of the kind mentioned at the beginning comprising a tube with two openings, which is displaceable on the first wire member, and in which the second wire member is also guided in a longitudinally displaceable manner is also known. In order to avail over the necessary spring path for activation of the retractor, the area of the first wire member carrying the pressure spring is of relatively long design, and since this area is bent approximately in the center, it tends to prick the gum when the retractor is being worn. Moreover, the tube with two openings is relatively large and causes an annoyance when worn. Finally, the first wire member engaging with the tooth which is to be corrected, is relatively rigid, whereas, in actual fact, as great a flexibility as possible is desired.

The object underlying the invention was to produce a retractor which despite an adequate path for the activation and desired flexibility of the wire member which engages with the tooth to be corrected, is smaller than the first above-described known retractor and cannot be as easily distorted in shape as the latter. In order to achieve this object a retractor of the kind mentioned at the beginning is designed in accordance with the invention such that the second wire member is attached to the tube having one opening, and in that the first wire member forms a spring comprising two legs and two turns (approximately 5×180°) located between said legs, the ends of said turns extending around approximately right-angled bends to issue in the wire member ends. Two things are achieved by combining such a spring with a helical spring: Firstly, the helical spring can be of shorter design, so that the area of the first wire member carrying the helical spring does not protrude as far from the longitudinal axis of the retractor, even when this area is bent. Furthermore, the desired flexibility of the first wire member is attained thereby. Nevertheless, the retractor according to the invention is more stable in the face of torsional stress than the known first above-described retractor. At the same time, the necessity of using a tube comprising two openings, as in the case of the second above-described known retractor, is eliminated.

The known retractors are made from a 0.41×0.41 mm four-edged steel wire. It has now become evident that the quality of the guidance of the two wire members along each other can be substantially improved if the first wire member consists of 0.41×0.41 mm four-edged wire, and the second wire member of 0.41×0.46 mm four-edged wire. Furthermore, in the case of the retractor according to the invention, the guidance play occurs only in one single tube, and not, as in the case of the known retractor of the kind mentioned at the beginning, in two tubes.

In a preferred embodiment of the retractor according to the invention, the springs are so designed that a tractive force of approximately 100 to 120 grams corresponds to an activation of the retractor by 2 mm, and a tractive force of approximately 140 grams corresponds to an activation of 3 mm.

Further features, details and advantages of the invention are to be found in the attached claims and/or the following description and enclosed drawings of a preferred embodiment of the retractor.

FIG. 1 is a side view of the retractor.
FIG. 2 is a plan view of the retractor.
FIG. 3 is a section along line 3—3 of FIG. 1.
Fig. 4 is a side view of the retractor shown in FIG. 1 attached to the tooth to be moved and a stationary tooth.

The invention relates to a cuspid retractor spring for edgewise brackets. This retractor is composed of a first and a second wire member 10 and 12, respectively, which are displaceable relative to each other in a longitudinal direction. At its front end, the first wire member comprises an eyelet 14 to prevent gum injuries. Adjoining said eyelet is a straight wire portion 16 for attachment to the tooth which is to be corrected. The wire portion 16 extends around an approximately right-angled bend 18 to issue in a leg 20 of a spring 22. As shown in FIG. 2, the spring 22 comprises two turns 22a and 22b, which issue in a further leg 24 of the spring 22, so that, in total, the wire has been turned around 5×180°. The leg 24 extends around a further, approximately right-angled bend 26 to issue in a slightly upwardly bent wire portion 30 comprising at its free end an eyelet 32 serving as the one abutment for a helical spring 34 mounted on the wire portion 30.

The other abutment is formed by a tube 36 which is displaceably guided on the wire portion 30. The tube 36 is pressed against the bend 26 by the helical spring 34. One end of the second wire member 12 is attached, more particularly, welded to the side of the tube 36 that faces away from the spring 22.

It is to be noted in connection with the section which is not shown in the correct scale in FIG. 3, that the first wire member should have a square cross-section, while the cross-section of the second wire member 12 should be rectangular.

In order to activate the retractor, the right end of the second wire member 12, as shown in FIGS. 1 and 2, is pulled so far to the right until the force acting upon the tooth to be corrected has reached the desired value, whereupon the second wire member is bent around an abutment to secure it. This abutment will normally be a tube attached to a band, with the second wire member passing through said tube. The aforementioned band is then placed around a tooth, more particularly, a molar.

More specifically, as shown in FIG. 4, wire portion 16 extends through tube 54 on band 52 which in turn is secured to cuspid 50 which is to be moved by the retractor. The end of wire member 12 remote from the spring 22 extends through tube 60 attached to band 58 which in turn is secured to a molar as explained above in connection with activating the retractor.

What I claim is:

1. An orthodontic appliance for moving a tooth comprising first and second wire members displaceable relative to each other in a longitudinal direction, a guiding member displaceably mounted on said first wire member, said second wire member having one portion secured to said guiding member and another portion for attachment to a stable tooth, said first wire member having a partial attachment to said tooth to be moved and another portion being displaceably guided along said second wire member by means of said guiding member, a helical pressure spring carried by said first wire member engaging said second wire member and said guide member for biasing said wire member for relative displacement, said first wire member forming a second spring for biasing said wire members and providing vertical flexibility, said second spring comprising two upwardly extending legs and more than one helical turn located between said legs.

2. An orthodontic appliance as claimed in claim 1 wherein said guiding member comprises a tube and the leg of the second spring that faces away from said second wire member forms a stop member for the tube.

3. An orthodontic appliance as claimed in claim 1 wherein the portion of said first wire member carrying the pressure spring is bent upwardly and outwardly, and said second wire member is attached to the side of said guiding member that faces away from the second spring.

4. An orthodontic appliance as claimed in claim 1 wherein said first wire member has a square cross-section and said second wire member has a rectangular cross-section.

5. An orthodontic appliance as claimed in claim 1 wherein the springs are so designed that a tractive force of approximately 100–120 grams corresponds to an activation of the appliance by 2 mm, and a tractive force of approximately 140 grams corresponds to an activation of 3 mm.

6. An orthodontic appliance as claimed in claim 1 wherein said more than one turn includes two turns comprising approximately $5 \times 180°$.

7. An orthodontic appliance as claimed in claim 4 wherein said first wire member has a cross-section of approximately $0.41 \times 0.41$ mm and said second wire has a cross-section of approximately $0.41 \times 0.46$ mm.

* * * * *